US009974686B2

(12) United States Patent
Easley et al.

(10) Patent No.: US 9,974,686 B2
(45) Date of Patent: May 22, 2018

(54) OPHTHALMIC SURGICAL FLUID HANDLING CASSETTE

(71) Applicant: SYNERGETICS, INC., O'Fallon, MO (US)

(72) Inventors: James Easley, O'Fallon, MO (US); John Boswell, O'Fallon, MO (US)

(73) Assignee: SYNERGETICS, INC., O'Fallon, MO (US)

( * ) Notice: Subject to any disclaimer, the term of this patent is extended or adjusted under 35 U.S.C. 154(b) by 678 days.

(21) Appl. No.: 14/411,336

(22) PCT Filed: Jun. 26, 2013

(86) PCT No.: PCT/US2013/047967
§ 371 (c)(1),
(2) Date: Dec. 24, 2014

(87) PCT Pub. No.: WO2014/004713
PCT Pub. Date: Jan. 3, 2014

(65) Prior Publication Data
US 2015/0335473 A1   Nov. 26, 2015

Related U.S. Application Data

(60) Provisional application No. 61/664,679, filed on Jun. 26, 2012.

(51) Int. Cl.
*A61F 9/007* (2006.01)
*A61M 1/00* (2006.01)

(52) U.S. Cl.
CPC ........... *A61F 9/007* (2013.01); *A61M 1/0001* (2013.01); *A61M 1/0058* (2013.01);
(Continued)

(58) Field of Classification Search
CPC ............... A61B 2217/005; A61F 9/007; A61F 9/00736; A61M 1/0001; A61M 1/00058;
(Continued)

(56) References Cited

U.S. PATENT DOCUMENTS

| 4,790,816 A | 12/1988 | Sundblom et al. |
| 2005/0065462 A1* | 3/2005 | Nazarifar ............ A61M 1/0031 604/30 |

(Continued)

FOREIGN PATENT DOCUMENTS

| WO | 2007/143677 A2 | 12/2007 |
| WO | 2012/170379 A1 | 12/2012 |

OTHER PUBLICATIONS

Extended European Search Report issued in corresponding European Application No. 13810732.1 dated Jun. 24, 2016. 11 pages.

(Continued)

*Primary Examiner* — Tatyana Zalukaeva
*Assistant Examiner* — Kai Weng
(74) *Attorney, Agent, or Firm* — Michael L. Smith

(57) ABSTRACT

An ophthalmic system (100) having an ophthalmic cassette (104) for operative engagement with an ophthalmic apparatus (102) is disclosed. The ophthalmic cassette (104) includes a cassette body (108) having a manifold (124) defining an inlet port (180) in fluid flow communication with first and second fluid pathways (120/122) which are in selective fluid flow communication with respective first and second storage chambers (116/118) such that fluid enters either the first storage chamber (116) or the second storage chamber (118). The ophthalmic apparatus (102) is operable to permit alternate fluid flow communication between the inlet port (108) and either the first storage chamber (116) or the second storage chamber (118) during operation of the ophthalmic system (100).

11 Claims, 6 Drawing Sheets

(52) U.S. Cl.
CPC ..... *A61B 2217/005* (2013.01); *A61F 9/00736* (2013.01); *A61M 2205/128* (2013.01); *A61M 2205/3389* (2013.01); *A61M 2210/0612* (2013.01); *F04C 2270/041* (2013.01)

(58) Field of Classification Search
CPC .... A61M 2205/128; A61M 2205/3389; A61M 2210/0612
See application file for complete search history.

(56) References Cited

U.S. PATENT DOCUMENTS

| | | |
|---|---|---|
| 2007/0287959 A1 | 12/2007 | Walter et al. |
| 2008/0114301 A1 | 5/2008 | Bandhauer et al. |
| 2010/0125257 A1 | 5/2010 | Perkins et al. |
| 2011/0190606 A1 | 8/2011 | Gable et al. |

OTHER PUBLICATIONS

International Search Report issued in International Application No. PCT/US2013/047967 dated Oct. 16, 2013.
Supplemental European Search Report dated Feb. 16, 2016 from corresponding European Patent Application No. 13810732. 6 pages.

\* cited by examiner

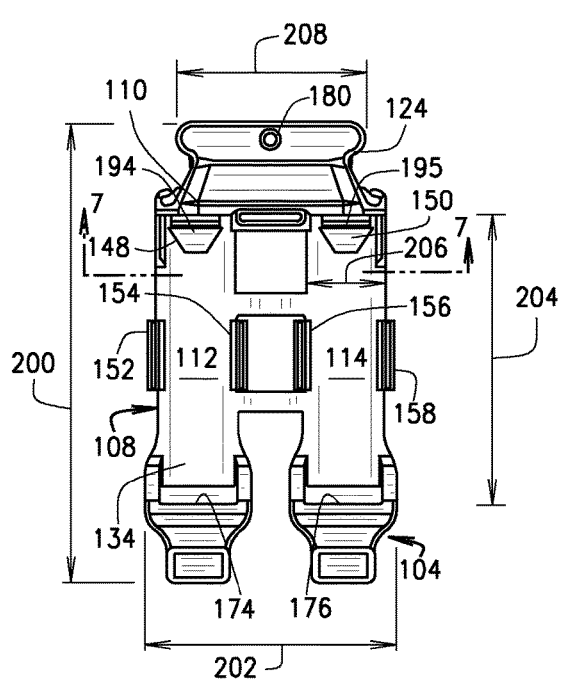
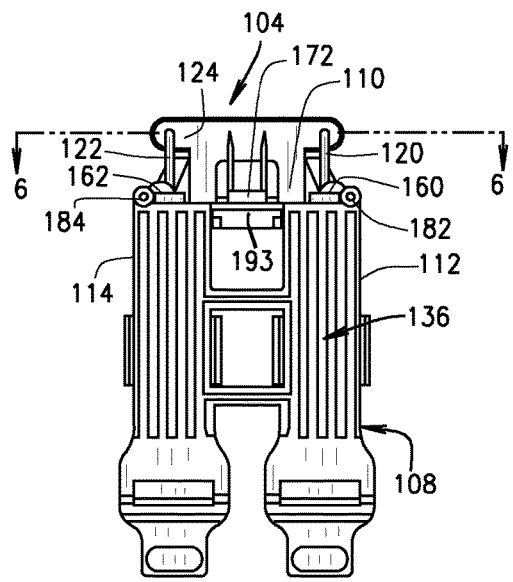
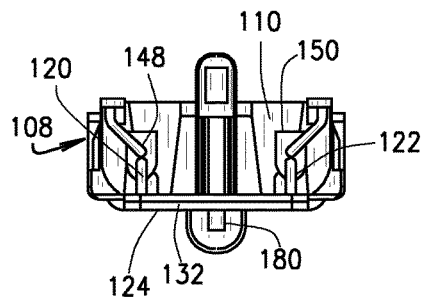
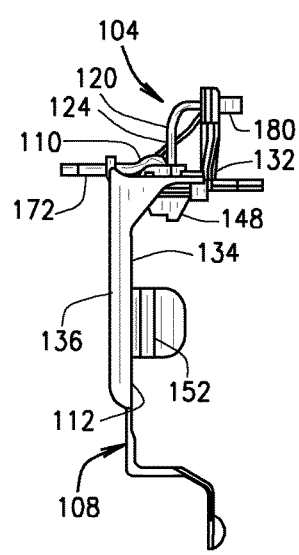
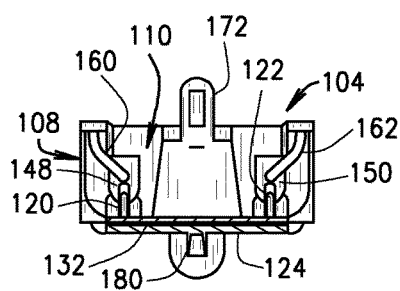
FIG. 2
FIG. 3
FIG. 4
FIG. 5
FIG. 6

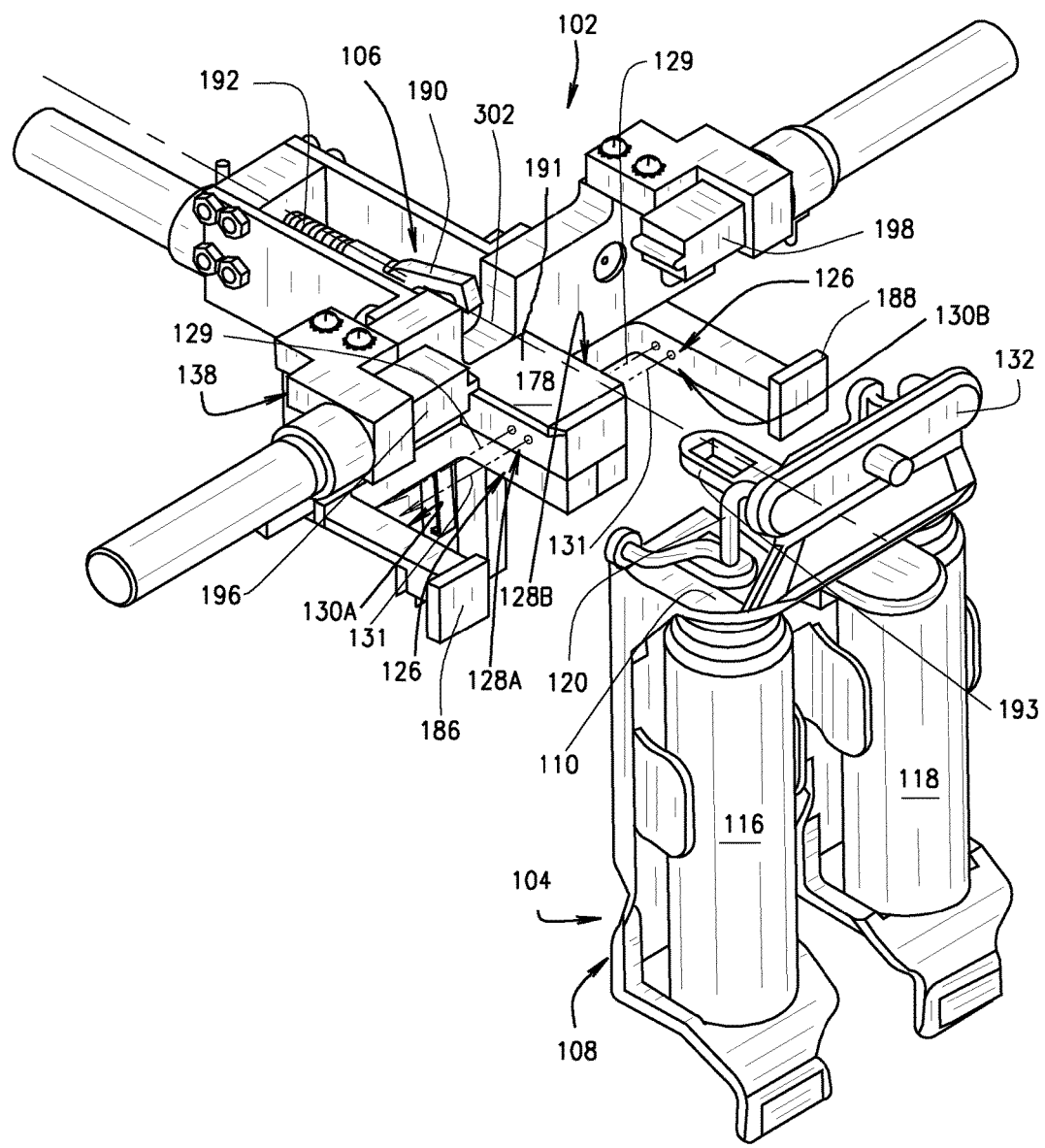
F I G . 1 0

OPHTHALMIC SURGICAL FLUID HANDLING CASSETTE

FIELD

The present document relates generally to an ophthalmic system, and in particular to an ophthalmic cassette operatively engaged to an ophthalmic apparatus that permits selective fluid flow communication through either a first fluid pathway or a second fluid pathway.

SUMMARY

In an embodiment, an ophthalmic cassette may include a cassette body having a manifold defining an inlet port in fluid flow communication with a first fluid pathway and a second fluid pathway. In addition, a first storage chamber is in selective fluid flow communication with the first fluid pathway and a second storage chamber is in selective fluid flow communication with the second fluid pathway, wherein the first fluid pathway and the second fluid pathway are configured to permit alternate fluid flow communication between the inlet port and either the first fluid inlet portion or the second fluid inlet portion such that either the first fluid pathway or the second fluid pathway is in fluid flow communication with the inlet port.

In another embodiment, an ophthalmic apparatus may include a housing defining a cassette receptacle, a sensor arrangement in operative communication with the cassette receptacle, and a cassette configured to operatively engage the cassette receptacle for establishing operative communication between the cassette and the sensor arrangement. The cassette may include a cassette body configured to engage the cassette receptacle, wherein the cassette body defines a storage receptacle, a manifold defining an inlet port in fluid flow communication with a fluid pathway, and a storage chamber in selective fluid flow communication with the fluid pathway when the storage chamber is engaged to the storage receptacle of the cassette body. In addition, the sensor arrangement is operatively associated with the cassette engaged to the cassette receptacle for transmitting a detection signal to detect: a first state wherein the storage chamber is detached from the storage receptacle, a second state wherein the storage chamber is attached to the storage receptacle and the sensor arrangement detects air in the storage chamber, and a third state wherein a liquid fills the storage chamber attached to the storage receptacle at a predetermined level.

In yet another embodiment, a method for manufacturing an ophthalmic cassette may include:
- forming a cassette body including at least one cassette receptacle and a manifold defining an inlet port in fluid flow communication with at least one fluid pathway; and
- forming at least one storage chamber associated with a respective one of the at least one cassette receptacle, wherein each of the at least one storage chamber is in fluid flow communication with a respective one of the at least one fluid pathway;
- wherein the at least one fluid pathway is operable to permit fluid flow communication between the inlet port and a respective one of at least one storage chamber.

In another embodiment, an ophthalmic cassette may include a cassette body defining a manifold and a receptacle having a storage chamber that is rigid and repeatedly attachable from the receptacle for establishing fluid flow communication between the manifold and the storage chamber.

Additional objectives, advantages and novel features will be set forth in the description which follows or will become apparent to those skilled in the art upon examination of the drawings and detailed description which follows.

BRIEF DESCRIPTION OF THE DRAWINGS

FIG. 2 is a front view of an ophthalmic cassette body of the ophthalmic cassette shown in FIG. 1;

FIG. 3 is a rear view of the ophthalmic cassette body;

FIG. 4 is a side view of the ophthalmic cassette body;

FIG. 5 is a top view of the ophthalmic cassette body showing the manifold in fluid flow communication with a first fluid pathway and a second fluid pathway;

FIG. 6 is a top cross-sectional view of the ophthalmic cassette body illustrating a manifold chamber of the manifold taken along line 6-6 of FIG. 3;

FIG. 10 is an isolated perspective view of a portion of a cassette receptacle for the ophthalmic apparatus shown in engaging alignment with the ophthalmic cassette;

Corresponding reference characters indicate corresponding respective elements among the view of the drawings. The headings used in the figures should not be interpreted to limit the scope of the claims.

DETAILED DESCRIPTION

Figure 1:
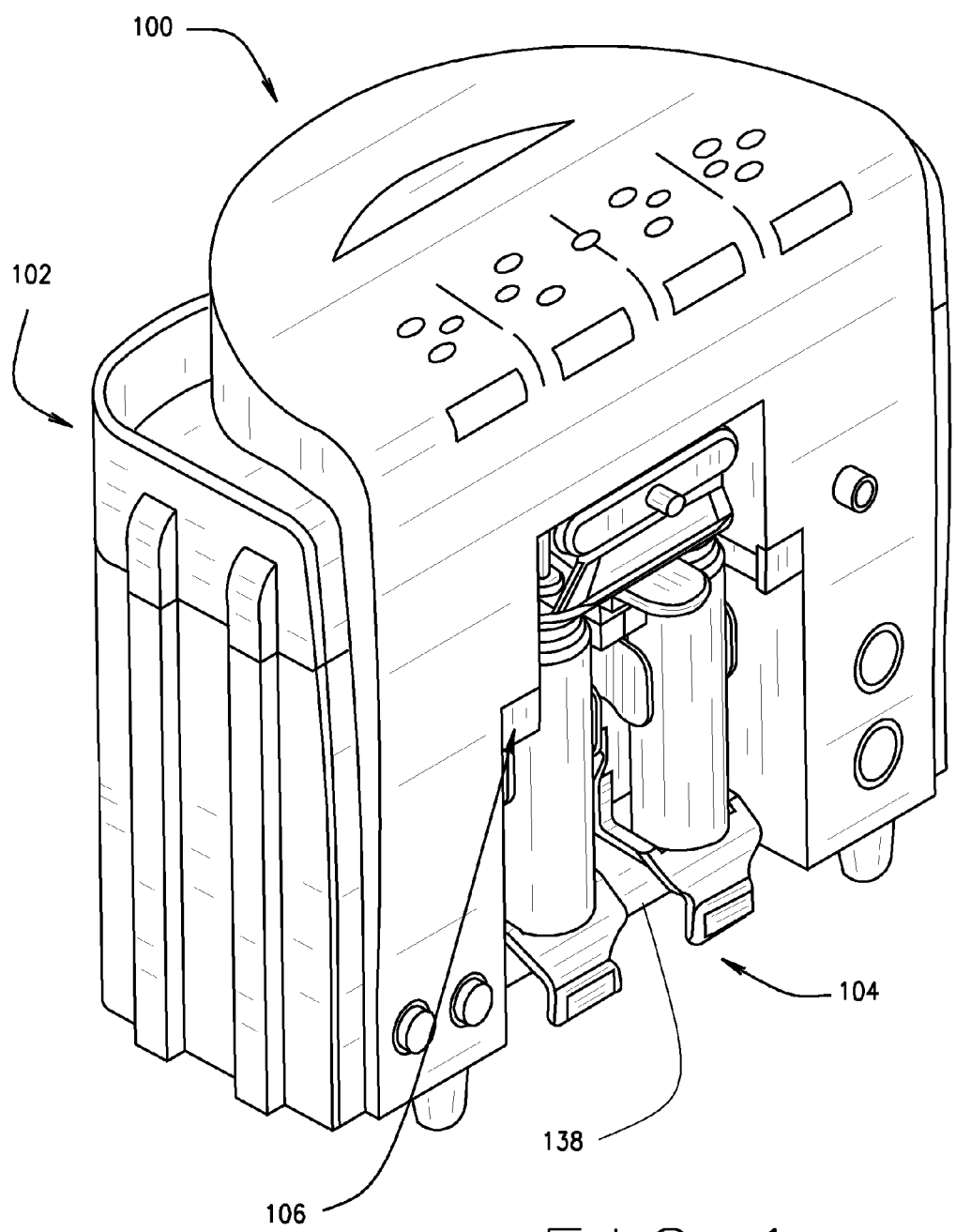
FIG. 1 is a perspective view of an ophthalmic system having an ophthalmic apparatus operatively engaged to an ophthalmic cassette.

An ophthalmic system having an improved ophthalmic cassette operatively engaged to an ophthalmic apparatus for performing one or more ophthalmic operations is described herein. Referring to the drawings, one embodiment of the ophthalmic system is illustrated and generally indicated as 100 in FIG. 1. As shown in FIG. 1, an embodiment of the ophthalmic system 100 may include an ophthalmic apparatus 102 having a latching mechanism 106 (FIGS. 10 and 11) that operatively engages the ophthalmic apparatus 102 to an ophthalmic cassette 104 as shall be described in greater detail below.

Figure 7:
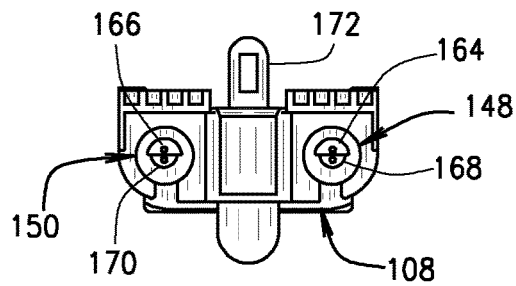
FIG. 7 is a bottom view of the ophthalmic cassette body taken along line 7-7 of FIG. 2.
Figure 9:
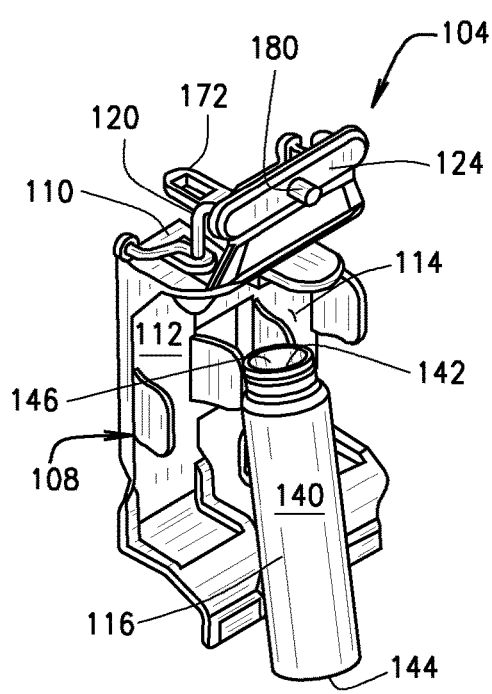
FIG. 9 is an exploded view of the ophthalmic cassette.
Figure 8:
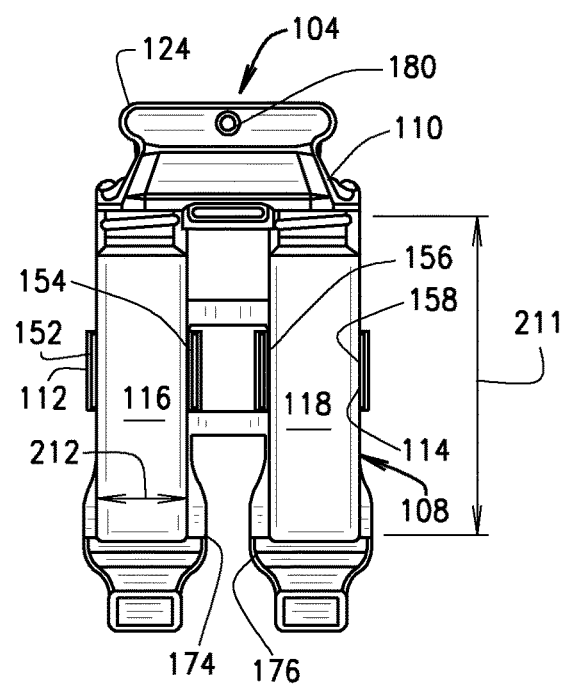
FIG. 8 is a front view of the ophthalmic cassette with first and second storage chambers engaged to first and second receptacles of the ophthalmic cassette body.

Referring to FIGS. 2-8, the ophthalmic cassette 104 includes a cassette body 108 having a top portion 110 with a manifold 124. The manifold 124 includes an inlet port 180 that permits the ingress of fluid from an ophthalmic instrument (not shown) positioned along a surgical site (not shown) into a manifold chamber 132 (FIG. 6) defined within the manifold 124. In some embodiments, the cassette body 108 further includes a first receptacle 112 and a second receptacle 114 sized and shaped to receive a first storage chamber 116 and the second storage chamber 118, respectively. In one embodiment shown in FIG. 9, first and second storage chambers 116 and 118 may be simply and repeatedly attached and detached to or from the respective first and second receptacles 112 and 114; however, in other embodiments the first and second storage chambers 116 and 118 may be integral with the cassette body 108 as shown in FIG. 8. Referring to FIGS. 8 and 9, in some embodiments the first and second storage chambers 116 and 118 may each have an elongated vial body 140 (FIG. 9) defining a hollow chamber 146 configured to store fluid and/or debris in which the hollow chamber 146 communicates with an open end 142 of the elongated vial body 140 for entry of fluid therein and a closed end 144 formed at the opposite end of the elongated vial body 140. In other embodiments, the elongated vial body 140 may have different shapes of cross-sectional configurations, such an oval, square, rectangular, hexagonal, irregular or non-geometric.

As shown in FIGS. 4-6, the manifold chamber 132 is in fluid flow communication with an inlet port 180 connected to an inlet pathway (not shown) that allows fluid flow into the ophthalmic cassette 104 from the ophthalmic instrument for storage in the first and/or second storage chambers 116 and 118. Referring to FIGS. 3, 5, and 6, first fluid pathway 120 and a second fluid pathway 122 establish selective fluid flow communication from the inlet port 180, through the manifold chamber 132 and to either the first storage chamber 116 (FIG. 8) or the second storage chamber 118 (FIG. 8). In one embodiment, flexible, hollow tubing may be used to form a portion of the first and second fluid pathways 120 and 122 as well first and second vacuum pathways 160 and 162, which apply negative gauge pressure to the ophthalmic cassette 104 as shall be discussed in greater detail below.

Referring to FIGS. 2 and 5-8, the top portion 110 of the cassette body 108 includes a first inlet portion 148 and a second inlet portion 150 that are aligned with the first receptacle 112 and the second receptacle 114, respectively. The first inlet portion 148 is in fluid flow communication with the first storage chamber 116 when the first storage chamber 116 is engaged to the first receptacle 112, while the second inlet portion 150 is in fluid flow communication with the second storage chamber 118 when the second storage chamber 118 is engaged to the second receptacle 114. As such, the first inlet portion 148 and the second inlet portion 150 permit fluid and debris from the manifold chamber 132 to enter either the first storage chamber 116 or the second storage chamber 118.

As shown in FIGS. 3, 5 and 6, in one embodiment the first inlet portion 148 is in fluid flow communication with the first fluid pathway 120 and a separate first vacuum pathway 160. As noted above, the first fluid pathway 120 acts as a pathway for fluid and debris into first storage chamber 116 from a surgical instrument as the first vacuum pathway 160 applies a negative gauge pressure to the first storage chamber 116 from a source of vacuum (not shown) through a first aspiration port 182 (FIG. 3) to draw in the fluid and debris therein. Similarly, the second inlet portion 150 is in fluid flow communication with the second fluid pathway 122 and a separate second vacuum pathway 162 that applies a negative gauge pressure to the second storage chamber 118 from a source of vacuum through a second aspiration port 184 (FIG. 3) to draw in fluid and debris.

Referring to FIGS. 4 and 7, the first inlet portion 148 defines a stepped configuration with a first fluid inlet 164 that allows fluid to enter the first storage chamber 116 and a first vacuum outlet 168 that applies a negative gauge pressure within the first storage chamber 116 for drawing fluid through the first fluid inlet 164. In some embodiments as shown in FIG. 7, the first vacuum outlet 168 is raised higher relative to the first fluid inlet 164 such that rising fluid within the first storage chamber 116 is not allowed to rise beyond the first fluid inlet 164, thereby preventing fluid from entering the first vacuum pathway 160. Similarly, as shown in FIG. 7, the second inlet portion 150 defines an identically-shaped stepped configuration with a second fluid inlet 166 that allows fluid to enter the second storage chamber 118 and a second vacuum outlet 170 that applies a negative gauge pressure for drawing fluid through the second fluid inlet 166.

Referring back to FIGS. 2 and 9, the first and second inlet portions 148 and 150 each define a plurality of raised circumferential flanges 194 and 195 configured to engage an inner surface defined along the open end 142 of the elongated vial body 140 for each of the first and second storage chambers 116 and 118 when engaged to the first and second receptacles 112 and 114, respectively. As used herein, the term "plurality" shall mean more than one of a kind. When the first and second storage chambers 116 and 118 are so engaged to the first and second inlet portions 148 and 150, a fluid tight seal is established between the elongated vial body 140 of each of the storage chambers 116 and 118 and the first and second receptacles 112 and 114, respectively.

As shown in FIGS. 2-4, the cassette body 108 defines a front surface 134 and a rear surface 136. The front surface 134 defines the first and second receptacles 112 and 114 that are sized and shaped to receive the first and second storage chambers 116 and 118, respectively. Referring to FIG. 2, the first receptacle 112 has a substantially elongated rectangular shape and is collectively bounded by the first and second side portions 152 and 154, the first inlet portion 148, and a first seat 174. As such, the first receptacle 112 is configured to engage the first storage chamber 116. Similarly, the second receptacle 176 has an identical elongated rectangular shape and is collectively bounded by the first and second side portions 156 and 158, the second inlet portion 150, and a second seat 176. As such, the second receptacle 114 is configured to engage the second storage chamber 118.

During engagement of the first storage chamber 116 to the first receptacle 112, the open end 142 of the elongated vial body 140 may be engaged to the first inlet portion 148 as described above in relation to FIG. 9 and the closed end 144 of the elongated vial body 140 engaged to the first seat 174 such that the elongated vial body 140 is engaged between the first and second side portions 152 and 154 as shown in FIG. 8. Similarly, the second storage chamber 118 may be engaged to the second receptacle 114 by engaging the open end 142 of the elongated vial body 140 for the second storage chamber 118 to the second inlet portion 150 and then engaging the closed end 144 of the elongated vial body 140 to the second seat 176 such that the elongated vial body 140 is engaged between the first and second side portions 156 and 158.

Figure 13:
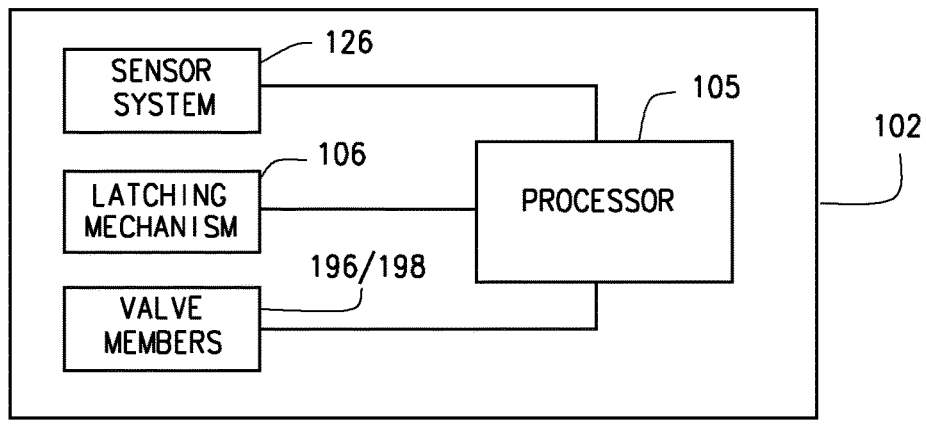
FIG. 13 is a simplified block diagram illustrating the processor and the other various components of the ophthalmic apparatus.

Referring to FIG. 13, in one embodiment the ophthalmic apparatus 102 may include a processor 105 for controlling the various operations of the ophthalmic system 100 (FIG. 1) including the ophthalmic cassette 104. In some embodiments, the processor 105 may be in operative association with a pair of valve members 196 and 198 for preventing or permitting fluid flow communication with the first and second storage chambers 116 and 118. In some embodiments, the processor 105 may control the latching mechanism 106 for operatively engaging the ophthalmic cassette 104 to the cassette receptacle 138 (FIG. 1) of the ophthalmic apparatus 102. Finally, in some embodiments the processor 105 may control the operation of a sensor system 126 for detecting the presence or absence of fluid in the first and second storage chambers 116 and 118. These functions of the processor 105 will be discussed in greater detail below.

Referring to FIG. 10, the ophthalmic apparatus 102 may include the first valve member 196 and the second valve member 198 for controlling the flow of fluid into the first and second storage chambers 116 and 118. In one embodiment, the first valve member 196 may be operatively associated with the first fluid pathway 120 for preventing or permitting fluid flow communication between the manifold chamber 132 and the first storage chamber 116, while the second valve member 198 may be operatively associated with the second fluid pathway 122 for preventing or permitting fluid flow communication between the manifold chamber 132 and the second storage chamber 118. In some embodiments, the first and second valve members 196 and 198 are controlled by the processor 105 (FIG. 13) such that fluid flow communication is established between the manifold chamber 132 and either the first storage chamber 116 or the second storage chamber 118. In some embodiments, the first and second valve members 196 and 198 may be pinch valves that occlude the first and second fluid pathways 120 and 122, respectively, to prevent fluid flow communication between the manifold chamber 132 and the first and second storage chambers 116 and 118, respectively, when the first and second valve members 196 and 198 are activated. When the first and second valve members 196 and 198 are deactivated, fluid flow communication is established between the manifold chamber 132 and the first and second storage chambers 116 and 118, respectively.

Figure 12:
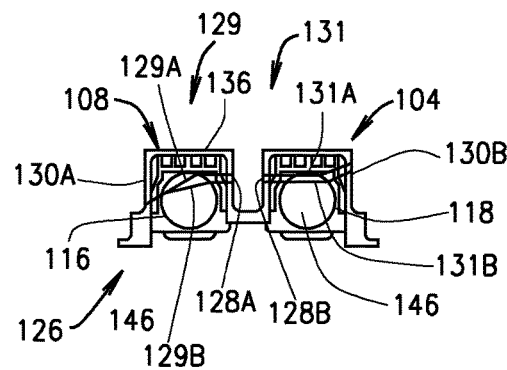
FIG. 12 is a top view of the ophthalmic cassette illustrating the sensor system and the various paths taken by respective optical detection beams through the first and second storage chambers, respectively.

As further shown in FIG. 10, the sensor system 126 detects the various states of the first and second storage chambers 116 and 118 using an optical detection system that transmits one or more optical detection signals 129 and 131 (FIG. 12). In a first state, the sensor system 126 may detect the absence of the first and second storage chambers 116 and 118 within the first and second receptacles 112 and 114. In a second state, the sensor system 126 may detect the presence of the first and second storage chambers 116 and 118 and the absence of a liquid in the first and second storage chambers 116 and 118 above a predetermined level within the first and second storage chambers 116 and 118, while in a third state the sensor system 126 may detect whether a liquid has risen to or above the predetermined level within the first and second storage chambers 116 and 118. In some embodiments, the term "predetermined level" means the level within the first and second storage chambers 116 and 118 which is equivalent to the same level of the optical detection signals 129A/B and 131A/B being transmitted and received by the sensor system 126 as illustrated in FIG. 12. For example, the sensor system 126 can detect whether the first and second storage chambers 116 and 118 are disengaged from the respective first and second receptacles 112 and 114; whether the first and second storage chambers 116 and 118 are engaged with the first and second receptacles 112 and 114, but not filled to a predetermined level with fluid; and whether the first and second storage chambers 116 and 118 are engaged with the respective first and second receptacles 112 and 114 and filled to or above a predetermined level with a liquid. In some embodiments, the sensor arrangement 126 may include a first pair of transmitters 128A operatively associated with the first storage chamber 116 for transmitting the pair of optical detection signals 129 to a first pair of receivers 130A for detecting the various states of the first storage chamber 116. Similarly, the sensor arrangement 126 may also include a second pair of transmitters 128B operatively associated with the second storage chamber 118 for transmitting a pair of optical detection signals 131 to a second pair of receivers 130B for detecting the various states of the second storage chamber 118.

Referring to FIG. 12, the operation of the sensor system 126 will be discussed in greater detail. In some embodiments, the first pair of transmitters 128A transmits first and second optical detection signals 129A and 129B through the first storage chamber 116 that are subsequently detected by the first pair of receivers 130A. Similarly, the second pair of transmitters 128B transmits first and second optical detection signals 131A and 131B through the second storage chamber 118 that are detected by the second pair of receivers 130B. For purposes of illustration, the respective paths taken by the first and second optical detection signals 129A and 129B are shown traveling through the first storage chamber 116 when filled with fluid to a predetermined level, while first and second optical detection signals 131A and 131B are shown traveling through the second storage chamber 118 when filled entirely with air or when fluid has not yet reached a predetermined level. Although not illustrated, the first and second optical detection signals 129A/B or 131A/B may also detect that the first or second storage chambers 116 and 118 are not engaged to respective first and second receptacles 112 and 114. In such a case, the travel of the optical detection signals 129A/B and 131A/B would be linear and not refracted between the transmitters 128A/B and receivers 130A/B.

In an embodiment, when the first and second storage chambers 116 and 118 are engaged within the first and second receptacles 112 and 114, respectively, one signal 129/131 is refracted by each of the first and second storage chambers 116 and 118 so that the signal 129/131 is detected by the sensor system 126. In an embodiment, when a liquid reaches the predetermined level in the first and second storage chambers 116 and 118 engaged within the first and second receptacles 112 and 114, respectively, neither signal 129/131 is received by the sensor system 126.

Referring back to FIGS. 1 and 10, the ophthalmic apparatus 102 may include a cassette receptacle 138 for operatively engaging the ophthalmic cassette 104 to the ophthalmic apparatus 102. As shown in FIG. 10, the cassette receptacle 138 may include a latching mechanism 106 having a claw member 190 configured to engage a tongue member 172 that extends laterally from the cassette body 108 substantially along latitudinal axis 302 (FIG. 11).

Figure 11:
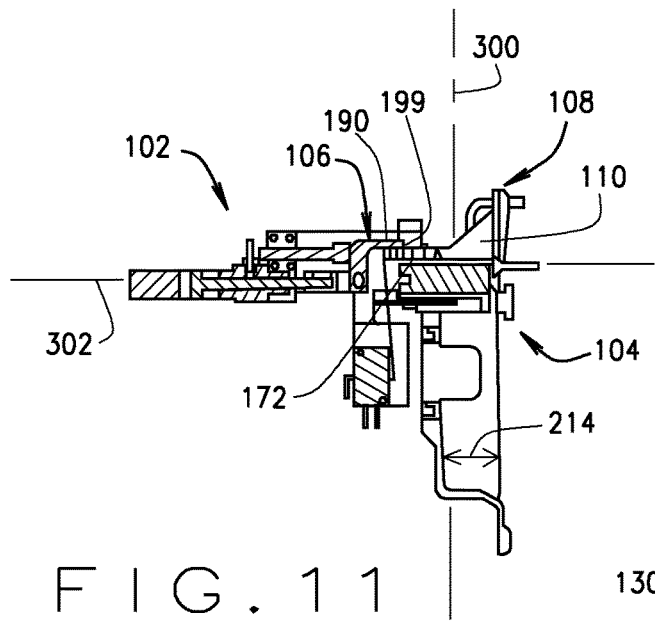
FIG. 11 is a cross-sectional view of the ophthalmic cassette engaged to the cassette receptacle of the ophthalmic apparatus.

As shown in FIG. 11, the claw member 190 defines a paw 199 at the free end of the claw member 190, which is configured to engage the tongue member 172 of the cassette body 108 when engaging the latching mechanism 106 to the ophthalmic cassette 104. To assist in guiding the cassette body 108 into operative engagement with the cassette receptacle 138, the ophthalmic apparatus 102 may include a guide 178 that extends laterally along latitudinal axis 302 transverse to longitudinal axis 300 for providing a structural lateral element that guides the tongue member 172 into operative engagement with the claw member 190.

As shown specifically in FIG. 10, the claw member 190 is operatively engaged to a spring 192 that spring loads the claw member 190 such that the claw member 190 must be lifted upwardly and the paw 199 is forced into engagement with the aperture defined by the tongue member 172. In some embodiments, the latching mechanism 106 may include first and second engagement members 186 and 188 that may engage both sides of the cassette body 108 such that the claw member 190 and first and second engagement members 186 and 188 collectively engage the ophthalmic cassette 104 to the ophthalmic apparatus 102. Referring to FIG. 10, in some embodiments the guide 178 may define a guide contacting surface 191 that is formed along the upper peripheral edge of the guide 178 that is configured to be engaged with a guide receiving surface 193 defined by the cassette body 108 when the latching mechanism 106 engages the ophthalmic cassette 104 to the ophthalmic apparatus 102.

Figure 15:
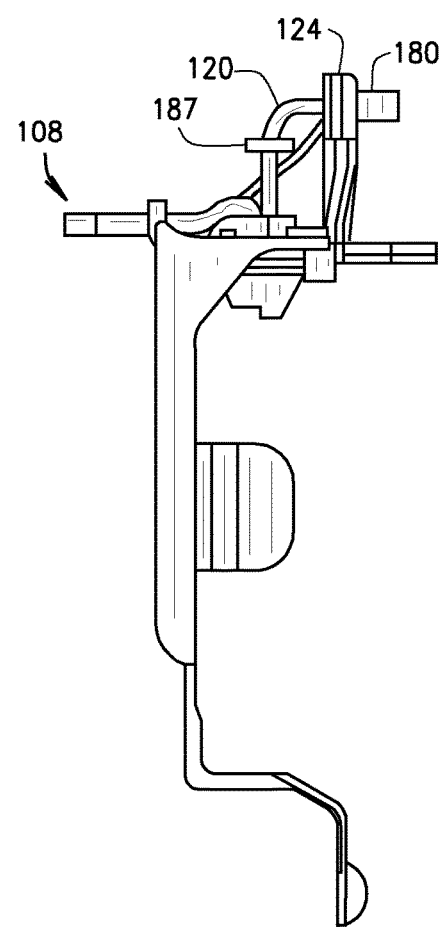
FIG. 15 is a side view of the ophthalmic cassette body showing an alternative embodiment of a valve member used to control fluid flow through the ophthalmic cassette.

Referring to FIG. 15, in an alternative embodiment of the cassette body 108 a pair of rotatable valve members 187 may be operatively controlled by the processor 105 (FIG. 13) for rotating each rotatable valve member 187 between an open position which allows for fluid flow through the first fluid pathway 120 or the second fluid pathway 122 (FIG. 5) and a closed position which allows for fluid flow communication through the first fluid pathway 120 or the second fluid pathway 122. In this arrangement, only one of the rotatable valve members 187 is in an open position for allowing fluid flow through either the first fluid pathway 120 or the second fluid pathway 122, but not simultaneous fluid flow through both first and second fluid pathways 120 and 122.

Figure 14:
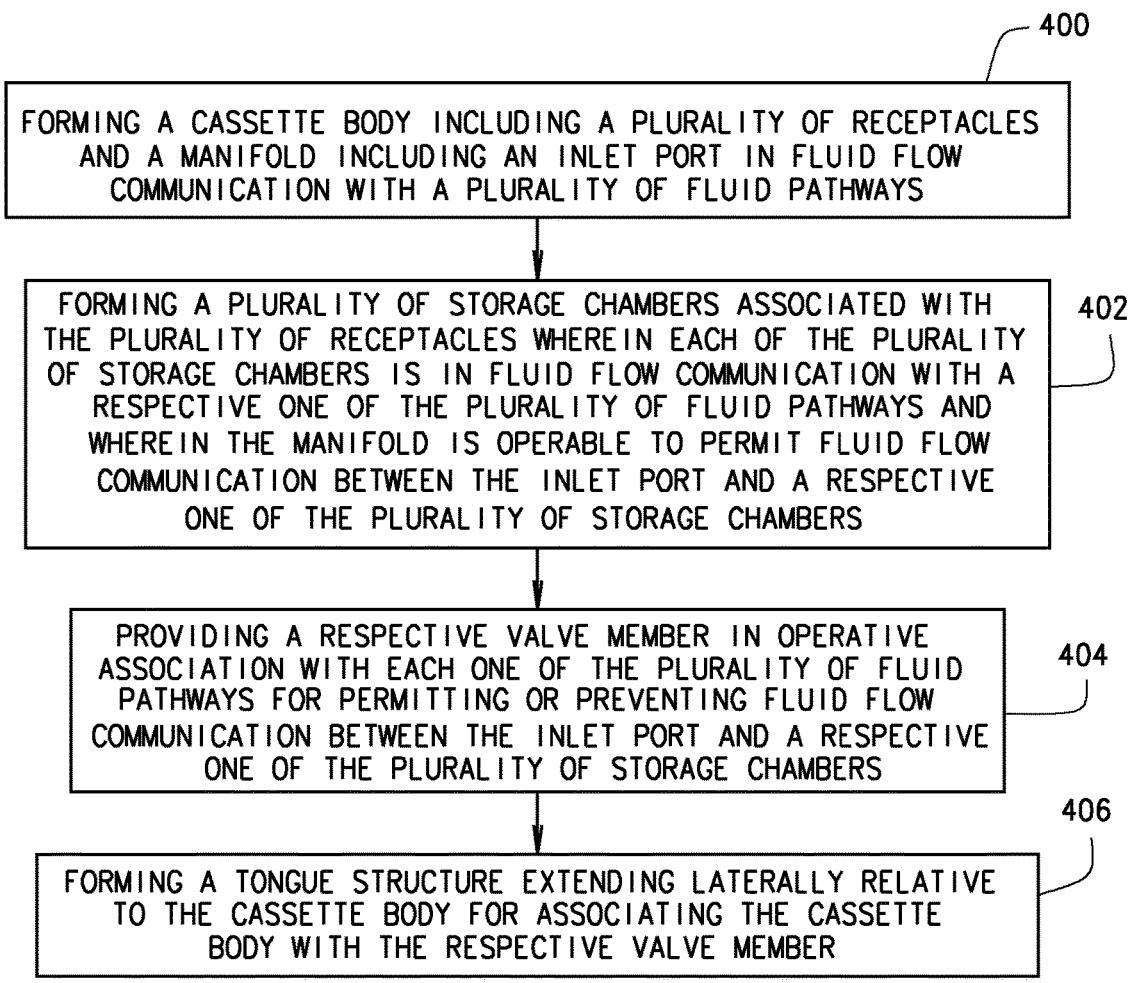
FIG. 14 is a flow chart illustrating a method for manufacturing the ophthalmic cassette.

In one embodiment, a method of manufacturing the ophthalmic cassette is illustrated in FIG. 14. At step 400, forming the cassette body 108 including first and second receptacles 112 and 114 and a manifold 124 defining an inlet port 180 in fluid flow communication with first and second fluid pathways 120 and 122. At step 402, forming first and second storage chambers 116 and 118 associated with the cassette body 108, wherein each of the first and second storage chambers 116 and 118 is in fluid flow communication with a respective one of the plurality of fluid pathways 120 and 122, and wherein the manifold 124 is operable to permit fluid flow communication between the inlet port 180 and a respective one of the first and second storage chambers 116 and 118. At step 404, providing a respective valve member 196 and 198 in operative association with each of the first and second fluid pathways 120 and 122 for permitting or preventing fluid flow communication between the inlet port 180 and a respective one of the first and second storage chambers 116 and 118. At step 406, forming a tongue member 172 extending laterally relative to the cassette body 108 for associating the cassette body 108 with the respective valve member 196 and 198.

In some embodiments, the ophthalmic cassette 104 may have the following dimensions during manufacture. The cassette body 108 may have a length 200 of about 16.5 cm and a width 202 of about 8.5 cm, while the manifold may have a length 208 of about 6.5 cm. In addition, the first and second receptacles 112 and 114 may each have a length 204 of about 11 cm and a width 206 of about 2.5 cm. In some embodiments, the volume of each of the first and second storage chambers 116 and 118 is about 50 ml. The first and second storage chambers 116 and 118 may have substantially the same length 204 and width 206 as shown for the first and second receptacles 112 and 114. However, the measurements above may be modified to other dimensions and still fall within the scope of the ophthalmic cassette 104.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. An ophthalmic cassette (104) comprising:
   a cassette body (108) comprising a manifold (124) defining an inlet port (180) in fluid flow communication with a first fluid pathway (120) that is in fluid flow communication with a first fluid inlet portion (148) and a second fluid pathway (122) that is in fluid flow communication with a second fluid inlet portion (150);
   wherein the first fluid pathway (120) and second fluid pathway (122) are configured to permit alternate fluid flow communication between the inlet port (180) and either the first fluid inlet portion (148) or the second fluid inlet portion (150) such that either the first fluid inlet portion (148) or the second fluid inlet portion (150) is in fluid flow communication with the inlet port (180),
   a first vacuum pathway (160) and a second vacuum pathway (162) in fluid flow communication with the first fluid inlet portion (148) and the second fluid inlet portion (150), respectively.

2. The ophthalmic cassette (104) of claim 1, further comprising:
   a first storage chamber (116) in selective fluid flow communication with the first fluid pathway (120); and
   a second storage chamber (118) in selective fluid flow communication with the second fluid pathway (122);
   wherein the manifold (124) is configured to permit fluid flow communication between the inlet port (180) and either the first fluid pathway (120) or the second fluid pathway (122) such that either the first storage chamber (116) or the second storage chamber (118) is in fluid flow communication with the inlet port (180).

3. The ophthalmic cassette (104) of claim 2, wherein the first storage chamber (116) and the second storage chamber (118) each define an elongated body (140) defining an open end (142) and a closed end (144).

4. The ophthalmic cassette (104) of claim 2, wherein first storage chamber (116) and the second storage chamber (118) are detachable from the cassette body (108).

5. The ophthalmic cassette (104) of claim 4, the cassette body (108) further comprising:
   a first receptacle (112) configured to receive the first storage chamber (116) for establishing fluid flow communication between the first storage chamber (116) and the first fluid pathway (120); and
   a second receptacle (114) configured to receive the second storage chamber (118) for establishing fluid flow communication between the second storage chamber (118) and the second fluid pathway (122).

6. The ophthalmic cassette (104) of claim 1, wherein when the first fluid pathway (120) is in fluid flow communication with the inlet port (180) the second fluid pathway (122) is not in fluid flow communication with the inlet port (180), and when the second fluid pathway (122) is in fluid flow communication with the inlet port (180) the first fluid pathway (120) is not in fluid flow communication with the inlet port (180).

7. The ophthalmic cassette (104) of claim 1, further comprising:
   a first valve member (187/196) in communication with the first fluid pathway (120) for preventing or permitting fluid flow communication between the first fluid pathway (120) and the first storage chamber (116); and
   a second valve member (187/198) in communication with the second fluid pathway (122) for preventing or permitting fluid flow communication between the second fluid pathway (122) and the second storage chamber (118).

8. The ophthalmic cassette (104) of claim 7, wherein the first valve member (187/196) and the second valve member (187/198) are configured to alternate between a closed position which prevents fluid flow communication and an open position for permitting fluid flow communication in alternating sequence relative to each other such that when the first valve member (187/196) is in the closed position, the second valve member (187/198) is in the open position and when the first valve member (187/196) is in the open position, the second valve member (187/198) is in the closed position.

9. The ophthalmic cassette (104) of claim 2, wherein the cassette body (108) is configured to be engaged to an apparatus (102) having a sensor system (126) for transmitting a detection signal (129/131) for detecting the presence or absence of a fluid in the first storage chamber (116) and the second storage chamber (118).

10. The ophthalmic cassette (104) of claim 9, wherein a portion of the first storage chamber (116) and a portion of the second storage chamber (118) is transparent to the detection signal (129/131).

11. The ophthalmic cassette (104) of claim 1, the cassette body (108) further comprising:
  a tongue member (172) extending from the cassette body (108), wherein the tongue member (172) is configured to engage a latching mechanism (106) of an apparatus (102) for engaging the ophthalmic cassette (104) to the apparatus (102).

\* \* \* \* \*